(12) United States Patent
Kumon et al.

(10) Patent No.: US 10,782,296 B2
(45) Date of Patent: Sep. 22, 2020

(54) ANTIBODY THAT SPECIFICALLY RECOGNIZES AND BINDS TO REIC/DKK-3 PROTEIN HAVING ACTIVE STRUCTURE AND MONITORING OF CANCER TREATMENT USING SUCH ANTI-REIC/DKK-3 ANTIBODY

(71) Applicants: National University Corporation Okayama University, Okayama-shi, Okayama (JP); Momotaro-Gene Inc., Okayama-shi, Okayama (JP)

(72) Inventors: Hiromi Kumon, Okayama (JP); Rie Kinoshita, Okayama (JP); Junichiro Futami, Okayama (JP)

(73) Assignees: National University Corporation Okayama University, Okayama (JP); Momotaro-Gene Inc., Okayama (JP)

( * ) Notice: Subject to any disclaimer, the term of this patent is extended or adjusted under 35 U.S.C. 154(b) by 106 days.

(21) Appl. No.: 15/763,535

(22) PCT Filed: Sep. 27, 2016

(86) PCT No.: PCT/JP2016/078339
§ 371 (c)(1),
(2) Date: Mar. 27, 2018

(87) PCT Pub. No.: WO2017/057308
PCT Pub. Date: Apr. 6, 2017

(65) Prior Publication Data
US 2018/0267040 A1   Sep. 20, 2018

(30) Foreign Application Priority Data
Sep. 28, 2015 (JP) ................. 2015-190401

(51) Int. Cl.
| | | |
|---|---|---|
| *G01N 33/574* | (2006.01) | |
| *C07K 16/18* | (2006.01) | |
| *C12N 5/12* | (2006.01) | |
| *C12N 15/02* | (2006.01) | |
| *G01N 33/53* | (2006.01) | |

(52) U.S. Cl.
CPC ........... *G01N 33/574* (2013.01); *C07K 16/18* (2013.01); *C12N 5/12* (2013.01); *C12N 15/02* (2013.01); *G01N 33/53* (2013.01); *C07K 2317/14* (2013.01)

(58) Field of Classification Search
CPC ...... G01N 33/574; G01N 33/53; C07K 16/18; C12N 5/12; C12N 15/02
USPC ...................................................... 435/7.23
See application file for complete search history.

(56) References Cited

U.S. PATENT DOCUMENTS

| 2006/0275263 A1 | 12/2006 | Namba et al. |
| 2012/0034251 A1 | 2/2012 | Kumon et al. |
| 2013/0267025 A1 | 10/2013 | Kumon et al. |

FOREIGN PATENT DOCUMENTS

| WO | WO 01/38528 A1 | 5/2001 |
| WO | WO 2009/119874 A1 | 10/2009 |
| WO | WO 2012/002582 A1 | 1/2012 |

OTHER PUBLICATIONS

International Search Report dated Dec. 27, 2016, in PCT/JP2016/078339.
Bafico et al., "Novel mechanism of Wnt signaling inhibition mediated by Dickkopf-1 interaction with LRP6/Arrow," Nature Cell Biotechnology, Jul. 2001, 3:683-686.
Hoang et al., "Dickkopf 3 Inhibits Invasion and Motility of Saos-2 Osteosarcoma Cells by Modulating the Wnt-ß-Catenin Pathway," Cancer Research, Apr. 15, 2004, 64:2734-2739.
Kumon et al., "Ad-REIC Gene Therapy: Promising Results in a Patient with Metastatic CRPC Following Chemotherapy," Clinical Medicine Insights Oncology, 2015, 9:31-38.
Kurose et al., "Decreased expression of REIC/Dkk-3 in Human Renal Clear Cell Carcinoma," The Journal of Urology, Mar. 2004, 171:1314-1318.
Moon et al., "The Promise and Perils of Wnt Signaling Through (ß-Catenin," Science, May 31, 2002, 296:1644-1646.
Nozaki et al., "Reduced expression of REIC/Dkk-3 gene in non-small cell lung cancer," International Journal of Oncology, 2001, 19:117-121.
Tsuji et al., "Antiproliferative Activity of REIC/Dkk-3 and Its Significant Down-Regulation of Non-Small-Cell Lung Carcinomas," Biochemical and Biophysical Research Communications, 2001, 289:257-263.

(Continued)

*Primary Examiner* — Yan Xiao
(74) *Attorney, Agent, or Firm* — Foley & Lardner LLP

(57) ABSTRACT

This invention provides an anti-REIC antibody that specifically recognizes a cancer-associated protein (REIC/Dkk-3) and enables monitoring of cancer treatment effects involving the use of the REIC/Dkk-3 gene or the REIC/Dkk-3 protein as a medicine. This invention also provides a method of diagnosis involving the use of such antibody. The method of diagnosis comprises a method of cancer detection comprising: measuring the REIC/Dkk-3 protein concentration in the biological sample obtained from a subject with the use of a first antibody or a functional fragment thereof that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient; and, when the REIC/Dkk-3 protein concentration in the biological sample obtained from the subject is lower than the REIC/Dkk-3 protein concentration in the biological sample from a healthy individual, determining that the subject is suffered from precancer or a neoplastic disease.

4 Claims, 10 Drawing Sheets
Specification includes a Sequence Listing.

(56) References Cited

OTHER PUBLICATIONS

Tsuji et al., "A REIC Gene Shows Down-Regulation in Human Immortalized Cells and Human Tumor-Derived Cell Lines," Biochemical and Biophysical Research Communications, 2000, 268:20-24.
Supplementary European Search Report dated Mar. 27, 2019, in EP 16851479.2.
Abarzua et al., "Heat Shock proteins play a crucial role in tumor-specific apoptosis by REIC/Dkk-3," International Journal of Molecular Medicine, 2007, vol. 20, pp. 37-43.
Supplementary European Search Report dated Mar. 23, 2019, in EP 16851479.2.

Fig. 1-1

| Antibody | Antigen | Reactivity | | | Recognition region |
|---|---|---|---|---|---|
| | | Full-length REIC/ Dkk-3 protein [Ala22-Ile350] | REIC partial region 1 [Arg142-Ile350] | REIC partial region 3 [Ser135-Phe288] | |
| N-1 | Full-length REIC/ Dkk-3 protein | + | - | - | N-terminal domain |
| N-2 | Full-length REIC/ Dkk-3 protein | + | - | - | N-terminal domain |
| C-1 | Full-length REIC/ Dkk-3 protein | + | + | - | C-terminal domain |
| C-2 | Full-length REIC/ Dkk-3 protein | + | + | - | C-terminal domain |
| Cys-1 | Full-length REIC/ Dkk-3 protein | + | + | + | Cysteine-rich domain |
| Cys-2 | Full-length REIC/ Dkk-3 protein | + | + | + | Cysteine-rich domain |
| Cys-3 | Full-length REIC/ Dkk-3 protein | + | + | + | Cysteine-rich domain |
| Cys-4 | REIC partial region 3 [Ser135-Phe288] | + | + | + | Cysteine-rich domain |
| Cys-5 | REIC partial region 3 [Ser135-Phe288] | + | + | + | Cysteine-rich domain |
| Cys-6 | REIC partial region 3 [Ser135-Phe288] | + | + | + | Cysteine-rich domain |
| Cys-7 | REIC partial region 3 [Ser135-Phe288] | + | + | + | Cysteine-rich domain |
| Cys-8 | REIC partial region 3 [Ser135-Phe288] | + | + | + | Cysteine-rich domain |

Fig. 4-2

| Patient No. | 3 | 5 | 7 | 8 | 9 |
|---|---|---|---|---|---|
| Age | 59 | 62 | 70 | 65 | 70 |
| Vector dose level | 1 | 2 | 3 | | |
| (vp) | $1 \times 10^{10}$ | $1 \times 10^{11}$ | $1 \times 10^{12}$ | | |
| Pre-treatment PSA | 15.75 | 11.1 | 16.18 | 9.82 | 14.19 |
| Clinical stage | B1 | B2 | C | B2 | C |
| Gleason Score | 4 + 4 | 5 + 5 | 4 + 5 | 4 + 4 | 4 + 4 |
| Nomogram Score | 124 | 140 | 167 | 127 | 161 |

Fig. 5

|  | Capture antibody | REIC protein concentration (ng/ml) | |
|---|---|---|---|
|  |  | 100 | 10 |
| Detection antibody: Biotin-labeled N-1 antibody | N-2 | 0.031 | 0.002 |
|  | C-1 | 0.364 | 0.071 |
|  | C-2 | 0.056 | 0.02 |
|  | Cys-1 | 0.484 | 0.165 |
|  | Cys-2 | 0.556 | 0.315 |
|  | Cys-3 | 0.675 | 0.413 |
|  | Cys-4 | 0.736 | 0.325 |
|  | Cys-5 | 0.400 | 0.104 |
|  | Cys-6 | 0.339 | 0.099 |

|  | Capture antibody | REIC protein concentration (ng/ml) | |
|---|---|---|---|
|  |  | 100 | 10 |
| Detection antibody: Biotin-labeled Cys-3 antibody | N-1 | 0.637 | 0.142 |
|  | N-2 | 0.086 | 0.008 |
|  | C-1 | 0.408 | 0.051 |
|  | C-2 | 0.122 | 0.014 |
|  | Cys-1 | 0.159 | 0.036 |
|  | Cys-2 | 0.199 | 0.108 |
|  | Cys-4 | 0.259 | 0.105 |
|  | Cys-5 | 0.193 | 0.041 |
|  | Cys-6 | 0.149 | 0.035 |

SEQUENCE LISTING

```
<160> NUMBER OF SEQ ID NOS: 2

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1 atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
                20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
            35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
        50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                85                  90                  95 gag acc aac aca gac acg aag gtt gga aat aat acc atc cat gtg cac     336
Glu Thr Asn Thr Asp Thr Lys Val Gly Asn Asn Thr Ile His Val His
                100                 105                 110 cga gaa att cac aag ata acc aac aac cag gct cga caa atg gtc ttt     384
Arg Glu Ile His Lys Ile Thr Asn Asn Gln Ala Arg Gln Met Val Phe
            115                 120                 125 tca gag aca gtt atc aca tct gtg gga gac gaa gaa ggc aga agg agc     432
Ser Glu Thr Val Ile Thr Ser Val Gly Asp Glu Glu Gly Arg Arg Ser
        130                 135                 140 cac gag tgc atc atc gac gag gac tgt ggg ccc agc atg tac tgc cag     480
His Glu Cys Ile Ile Asp Glu Asp Cys Gly Pro Ser Met Tyr Cys Gln
145                 150                 155                 160
```

-continued

| | | | | | | | | | | | | | | | | |
|---|---|---|---|---|---|---|---|---|---|---|---|---|---|---|---|---|
| ttt | gcc | agc | ttc | cag | tac | acc | tgc | cag | cca | tgc | cgg | ggc | cag | agg | atg | 528 |
| Phe | Ala | Ser | Phe | Gln | Tyr | Thr | Cys | Gln | Pro | Cys | Arg | Gly | Gln | Arg | Met | |
| | | | | 165 | | | | 170 | | | | | 175 | | | |
| ctc | tgc | acc | cgg | gac | agt | gag | tgc | tgt | gga | gac | cag | ctg | tgt | gtc | tgg | 576 |
| Leu | Cys | Thr | Arg | Asp | Ser | Glu | Cys | Cys | Gly | Asp | Gln | Leu | Cys | Val | Trp | |
| | | | 180 | | | | | 185 | | | | | 190 | | | |
| ggt | cac | tgc | acc | aaa | atg | gcc | acc | agg | ggc | agc | aat | ggg | acc | atc | tgt | 624 |
| Gly | His | Cys | Thr | Lys | Met | Ala | Thr | Arg | Gly | Ser | Asn | Gly | Thr | Ile | Cys | |
| | | 195 | | | | | 200 | | | | | 205 | | | | |
| gac | aac | cag | agg | gac | tgc | cag | ccg | ggg | ctg | tgc | tgt | gcc | ttc | cag | aga | 672 |
| Asp | Asn | Gln | Arg | Asp | Cys | Gln | Pro | Gly | Leu | Cys | Cys | Ala | Phe | Gln | Arg | |
| 210 | | | | | 215 | | | | | 220 | | | | | | |
| ggc | ctg | ctg | ttc | cct | gtg | tgc | ata | ccc | ctg | ccc | gtg | gag | ggc | gag | ctt | 720 |
| Gly | Leu | Leu | Phe | Pro | Val | Cys | Ile | Pro | Leu | Pro | Val | Glu | Gly | Glu | Leu | |
| 225 | | | | | 230 | | | | | 235 | | | | | 240 | |
| tgc | cat | gac | ccc | gcc | agc | cgg | ctt | ctg | gac | ctc | atc | acc | tgg | gag | cta | 768 |
| Cys | His | Asp | Pro | Ala | Ser | Arg | Leu | Leu | Asp | Leu | Ile | Thr | Trp | Glu | Leu | |
| | | | | 245 | | | | | 250 | | | | | 255 | | |
| gag | cct | gat | gga | gcc | ttg | gac | cga | tgc | cct | tgt | gcc | agt | ggc | ctc | ctc | 816 |
| Glu | Pro | Asp | Gly | Ala | Leu | Asp | Arg | Cys | Pro | Cys | Ala | Ser | Gly | Leu | Leu | |
| | | | 260 | | | | | 265 | | | | | 270 | | | |
| tgc | cag | ccc | cac | agc | cac | agc | ctg | gtg | tat | gtg | tgc | aag | ccg | acc | ttc | 864 |
| Cys | Gln | Pro | His | Ser | His | Ser | Leu | Val | Tyr | Val | Cys | Lys | Pro | Thr | Phe | |
| | | 275 | | | | | 280 | | | | | 285 | | | | |
| gtg | ggg | agc | cgt | gac | caa | gat | ggg | gag | atc | ctg | ctg | ccc | aga | gag | gtc | 912 |
| Val | Gly | Ser | Arg | Asp | Gln | Asp | Gly | Glu | Ile | Leu | Leu | Pro | Arg | Glu | Val | |
| | 290 | | | | | 295 | | | | | 300 | | | | | |
| ccc | gat | gag | tat | gaa | gtt | ggc | agc | ttc | atg | gag | gag | gtg | cgc | cag | gag | 960 |
| Pro | Asp | Glu | Tyr | Glu | Val | Gly | Ser | Phe | Met | Glu | Glu | Val | Arg | Gln | Glu | |
| 305 | | | | | 310 | | | | | 315 | | | | | 320 | |
| ctg | gag | gac | ctg | gag | agg | agc | ctg | act | gaa | gag | atg | gcg | ctg | ggg | gag | 1008 |
| Leu | Glu | Asp | Leu | Glu | Arg | Ser | Leu | Thr | Glu | Glu | Met | Ala | Leu | Gly | Glu | |
| | | | | 325 | | | | | 330 | | | | | 335 | | |
| cct | gcg | gct | gcc | gcc | gct | gca | ctg | ctg | gga | ggg | gaa | gag | att | tag | | 1053 |
| Pro | Ala | Ala | Ala | Ala | Ala | Leu | Leu | Gly | Gly | Glu | Glu | Ile | | | | |
| | | 340 | | | | | 345 | | | | | 350 | | | | |

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Val Glu Asp Thr Gln His Lys
    50                  55                  60

Leu Arg Ser Ala Val Glu Glu Met Glu Ala Glu Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
        115                 120                 125

```
Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
            340                 345                 350
```

ANTIBODY THAT SPECIFICALLY RECOGNIZES AND BINDS TO REIC/DKK-3 PROTEIN HAVING ACTIVE STRUCTURE AND MONITORING OF CANCER TREATMENT USING SUCH ANTI-REIC/DKK-3 ANTIBODY

TECHNICAL FIELD

The present invention relates to monitoring of cancer treatment effects and companion diagnostics using the REIC/Dkk-3 gene and the REIC/Dkk-3 protein. The present invention also relates to an anti-REIC/Dkk-3-specific antibody that enables prediction of cancer and determination of prognosis using the REIC/Dkk-3 protein as a tumor marker and a test method using the same. Specifically, the present invention relates to the anti-REIC/Dkk-3 antibody that can specifically recognize the REIC/Dkk-3 active structure and the method of diagnosis using the same.

BACKGROUND ART

The REIC/Dkk-3 gene is known to be associated with cell immortalization, and expression of such gene is suppressed in cancer cells (see Patent Literature 1 and Non-Patent Literatures 1 to 4).

The REIC/Dkk-3 gene is a Dkk family member and it inhibits Wnt signal transmission with the aid of a Wnt receptor (see Non-Patent Literatures 5 and 6). The Wnt gene plays multiple roles in biologically critical situations, such as cell growth, differentiation, and canceration (see Non-Patent Literatures 5 and 7).

When the full-length REIC/Dkk-3 protein is added to a culture solution in which peripheral blood mononuclear cells (monocytes) are cultured at 10 µg/ml, such cells are differentiated into dendritic cell-like cells (see Patent Literature 2).

In animal experiments, also, significant tumor contraction effects are attained via administration of the full-length REIC/Dkk-3 protein and a fragment peptide thereof to mouse models of tumors (see Patent Literature 3).

In addition, adenovirus-based REIC/Dkk-3 gene therapy resulted in complete response (complete remission) in the case of metastatic castration-resistant prostate cancer of a human (see Non-Patent Literature 8).

CITATION LIST

Patent Literature

Patent Literature 1: WO 2001/038528
Patent Literature 2: WO 2009/119874
Patent Literature 3: WO 2012/002582

Non Patent Literature

Non Patent Literature 1: Tsuji, T. et al., BiochemBiophys. Res. Commun., 268, 20-4, 2000
Non Patent Literature 2: Tsuji, T. et al., BiochemBiophys. Res. Commun., 289, 257-63, 2001
Non Patent Literature 3: Nozaki, I. et al., Int. J. Oncol., 19, 117-21, 2001
Non Patent Literature 4: Kurose, K. et al., J. Urol., 171, 1314-8, 2004
Non Patent Literature 5: Bafico, A. et al., Nat. Cell Biol., 3, 683-6, 2001
Non Patent Literature 6: Hoang, B. H. et al., Cancer Res., 64, 2734-9, 2004
Non Patent Literature 7: Moon, R. T. et al., Science 296, 1644-6, 2002
Non Patent Literature 8: Kumon, H. et al., Clin. Med. Insights Oncol., 23; 9, 31-38, 2015

SUMMARY OF INVENTION

Technical Problem

The present invention provides a method of monitoring cancer treatment effects using the REIC/Dkk-3 gene and REIC/Dkk-3 protein medicine by a diagnostic method that utilizes the anti-REIC/Dkk-3 antibody that can specifically recognize the REIC/Dkk-3 protein. The present invention further provides a method of prediction of cancer and determination of prognosis using the REIC/Dkk-3 protein as a tumor marker.

Solution to Problem

The present inventors have conducted concentrated studies concerning cancer gene therapy using the REIC/Dkk-3 gene and discovered that administration of the REIC/Dkk-3 gene incorporated into an expression vector to an organism would be remarkably effective for cancer treatment.

Also, the present inventors elucidated the role of the full-length REIC/Dkk-3 protein in a wide variety of immunological and inflammatory diseases in vivo and usefulness and advantages of the full-length REIC/Dkk-3 protein in treatment of such diseases (WO 2009/119874).

The present inventors have further examined a fragment peptide of the REIC/Dkk-3 protein and discovered that a particular partial region had strong physiological activity of inducing monocytes to differentiate into dendritic-cell-like cells and such physiological activity would be at least equivalent to that of the full-length REIC/Dkk-3 protein. This indicates that a particular partial region of the REIC/Dkk-3 protein is capable of inducing monocytes to differentiate into dendritic-cell-like cells, it activates cancer immunity, and it can be used for cancer treatment and prevention (WO 2012/002582).

The present inventors have also attempted to obtain various anti-REIC/Dkk-3 monoclonal antibodies and develop a method of assay for the REIC/Dkk-3 protein in the blood. They then examined the method of monitoring cancer treatment by such assay method and the use of the REIC/Dkk-3 protein as a biomarker for prediction of cancer and determination of prognosis.

As a result, the present inventors discovered that use of the novel anti-REIC/Dkk-3 monoclonal antibody would enable specific detection of a particular REIC/Dkk-3 protein molecular species in the blood, detection of such particular REIC/Dkk-3 protein molecular species would enable monitoring of cancer treatment and prediction of cancer and determination of prognosis, and the particular REIC/Dkk-3 protein molecular species could be used as a biomarker for monitoring of cancer treatment, prediction of cancer, and determination of prognosis.

Specifically, they selected, from among the newly obtained anti-REIC/Dkk-3 monoclonal antibodies, antibodies with very low reactivity with the REIC/Dkk-3 protein molecular species that is present at a high level in the blood from a cancer patient and capable of specifically binding to the particular REIC/Dkk-3 protein molecular species appearing after REIC/Dkk-3 treatment or surgical treatment.

They then discovered that sandwich-ELISA employing such antibodies could be used for monitoring of cancer treatment and as an assay system for prediction of cancer and determination of prognosis. This has led to the completion of the present invention.

Specifically, the present invention is as described below.

[1] A method of detecting cancer comprising measuring the REIC/Dkk-3 protein concentration in a biological sample obtained from a subject using a first antibody or a functional fragment thereof that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient and evaluating that the subject is suffered from precancer or a neoplastic disease when the REIC/Dkk-3 protein concentration in the biological sample from the subject is lower than the REIC/Dkk-3 protein concentration in the biological sample obtained from a healthy individual.

[2] The method of detecting cancer according to [1] comprising measuring the REIC/Dkk-3 protein concentration in a biological sample obtained from a subject using a second antibody or a functional fragment thereof that specifically recognizes the REIC/Dkk-3 protein having an active structure produced by a normal cell and the REIC/Dkk-3 protein existing at a high level in the blood from a cancer patient, determining the ratio of the concentration measured with the use of the first antibody or a functional fragment thereof relative to the concentration measured with the use of the second antibody or a functional fragment thereof, and evaluating that the subject is suffered from precancer or a neoplastic disease when the ratio is lower than the ratio determined with the use of a biological sample obtained from a healthy individual.

[3] The method of detecting cancer according to [1] or [2], wherein the first antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is an antibody that specifically recognizes the N-terminal domain of the REIC/Dkk-3 protein.

[4] The method of detecting cancer according to [2] or [3], wherein the second antibody that specifically recognizes the REIC/Dkk-3 protein having an active structure produced by a normal cell and the REIC/Dkk-3 protein existing at a high level in the blood from a cancer patient is an antibody that recognizes the cysteine-rich domain of the REIC/Dkk-3 protein.

[5] The method of detecting cancer according to any of [1] to [4], wherein the first antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is a monoclonal antibody that recognizes the N-terminal domain of the REIC/Dkk-3 protein produced by the hybridoma deposited internationally under Accession Number NITE BP-02103 (the N-1 antibody) and the second antibody that specifically recognizes the REIC/Dkk-3 protein having an active structure produced by a normal cell and the REIC/Dkk-3 protein existing at a high level in the blood from a cancer patient is a monoclonal antibody that recognizes the cysteine-rich domain of the REIC/Dkk-3 protein produced by the hybridoma deposited internationally under Accession Number NITE BP-02104 (the Cys-3 antibody).

[6] A method of monitoring cancer treatment comprising measuring the REIC/Dkk-3 protein concentration in the biological sample obtained from a patient under cancer treatment with time using a first antibody or a functional fragment thereof that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient, and when the REIC/Dkk-3 protein concentration is elevated, determining that cancer treatment activity or effects is approved.

[7] The method of monitoring according to [6], comprising measuring the REIC/Dkk-3 protein concentration in the biological sample obtained from a subject with time using the second antibody or a functional fragment thereof that specifically recognizes the REIC/Dkk-3 protein having an active structure produced by a normal cell and the REIC/Dkk-3 protein existing at a high level in the blood from a cancer patient, and determining the ratio of the concentration measured with the use of the first antibody relative to the concentration measured with the use of the second antibody, and determining that the cancer treatment activity or effects are approved when the ratio is elevated.

[8] The method of monitoring according to [6] or [7], wherein the biological sample obtained with time includes the biological samples obtained before, during, and after cancer treatment.

[9] The method of monitoring according to any of [6] to [8], wherein the cancer treatment involves the use of the REIC/Dkk-3 gene, a REIC/Dkk-3 gene fragment, the REIC/Dkk-3 protein, or a REIC/Dkk-3 peptide fragment.

[10] The method of monitoring according to any of [6] to [9], wherein the first antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is an antibody that specifically recognizes the N-terminal domain of the REIC/Dkk-3 protein.

[11] The method of monitoring according to any of [7] to [10], wherein the second antibody that specifically recognizes the REIC/Dkk-3 protein having an active structure produced by a normal cell and the REIC/Dkk-3 protein existing at a high level in the blood from a cancer patient is an antibody that recognizes the cysteine-rich domain of the REIC/Dkk-3 protein.

[12] The method of monitoring according to any of [6] to [11], wherein the first antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is a monoclonal antibody that recognizes the N-terminal domain of the REIC/Dkk-3 protein produced by the hybridoma deposited internationally under Accession Number NITE BP-02103 (the N-1 antibody) and the second antibody that specifically recognizes the REIC/Dkk-3 protein having an active structure produced by a normal cell and the REIC/Dkk-3 protein existing at a high level in the blood from a cancer patient is a monoclonal antibody that recognizes the cysteine-rich domain of the REIC/Dkk-3 protein produced by the hybridoma deposited internationally under Accession Number NITE BP-02104 (the Cys-3 antibody).

[13] An antibody that recognizes the N-terminal domain of the REIC/Dkk-3 protein, an antibody that recognizes the cysteine-rich domain of the REIC/Dkk-3 protein, an antibody that recognizes the C-terminal domain of the REIC/Dkk-3 protein, or a functional fragment of any of such antibodies used for the method of detecting cancer according to any of [1] to [5] or the method of monitoring according to any of [6] to [12].

[14] A hybridoma deposited internationally under Accession Number NITE BP-02103 that produces the N-1 antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient.

[15] The N-1 antibody, which is a monoclonal antibody produced by the hybridoma according to [14], or a functional fragment thereof.

[16] A hybridoma deposited internationally under Accession Number NITE BP-02104 that produces the Cys-3 antibody that specifically recognizes the REIC/Dkk-3 protein having an active structure produced by a normal cell and the REIC/Dkk-3 protein existing at a high level in the blood from a cancer patient.

[17] The Cys-3 antibody, which is a monoclonal antibody produced by the hybridoma according to [16], or a functional fragment thereof.

[18] A test kit used for the method of detecting cancer according to any of [2] to [5] or the method of monitoring according to any of [7] to [12] comprising the antibody that recognizes the N-terminal domain of the REIC/Dkk-3 protein and the antibody that recognizes the cysteine-rich domain of the REIC/Dkk-3 protein or the antibody that recognizes the C-terminal domain of the REIC/Dkk-3 protein according to [13].

[19] A test kit used for the method of detecting cancer according to any of [2] to [5] or the method of monitoring according to any of [7] to [12] comprising the N-1 antibody according to [15] and the Cys-3 antibody according to [17].

This description includes part or all of the content as disclosed in the description and/or drawings of Japanese Patent Application No. 2015-190401, which is a priority document of the present application.

Advantageous Effects of Invention

According to the method of measurement of the REIC/Dkk-3 protein concentration using an anti-REIC/Dkk-3 protein antibody according to the present invention, monitoring of cancer treatment effects involving the use of the REIC/Dkk-3 gene or the REIC/Dkk-3 protein as a medicine can be carried out, the REIC/Dkk-3 protein detected by such method can serve as a useful biomarker for prediction of cancer and determination of prognosis, and such method can be used as companion diagnostics.

BRIEF DESCRIPTION OF DRAWINGS

FIG. 1-2 schematically shows the REIC/Dkk-3 protein structure.

FIG. 2 shows a standard curve prepared with the use of the standard REIC/Dkk-3 protein at 8 different concentrations (i.e., 0, 31.3, 62.5, 125, 250, 500, 1,000, and 2,000 pg/ml) (the recombinant REIC/Dkk-3 protein) in the sandwich ELISA method using the N-1 antibody that recognizes the N-terminal domain of the REIC/Dkk-3 protein as a capture antibody and the biotin-labeled anti-REIC/Dkk-3 polyclonal antibody as a detection antibody.

FIG. 3-1 shows the results of monitoring of REIC/Dkk-3 gene therapy by measuring the REIC/Dkk-3 protein concentration in the serum samples obtained from prostate cancer patients via sandwich ELISA. The standard serum samples (before treatment) and serum samples 1, 2, 7, and 14 days after the first treatment (immediately before the second treatment), 15, 17, 21, 28, and 56 days after the first treatment (immediately before surgery), and 84 days after the first treatment were subjected to the measurement. The results of measurement concerning Patient A (FIG. 3-1A) and Patient B (FIG. 3-1B) obtained with the use of the N-1 antibody that recognizes the N-terminal domain of the REIC/Dkk-3 protein as a capture antibody are shown.

FIG. 3-2 shows the results of monitoring of REIC/Dkk-3 gene therapy by measuring the REIC/Dkk-3 protein concentration in the serum samples obtained from prostate cancer patients via sandwich ELISA. The standard serum samples (before treatment) and serum samples 1, 2, 7, and 14 days after the first treatment (immediately before the second treatment), 15, 17, 21, 28, and 56 days after the first treatment (immediately before surgery), and 84 days after the first treatment were subjected to the measurement. The results of measurement concerning Patient A (FIG. 3-2A) and Patient B (FIG. 3-2B) obtained with the use of the Cys-3 antibody that recognizes the cysteine-rich domain as a capture antibody are shown.

FIG. 3-3 shows the ratio (%) of the REIC/Dkk-3 protein concentration measured with the use of the N-1 antibody relative to that measured with the use of the Cys-3 antibody as capture antibodies (N-1 antibody/Cys-3 antibody) concerning Patient A (FIG. 3-3A) and Patient B (FIG. 3-3B). As is apparent from the figures, treatment monitoring can be carried out using the concentration ratio measured with the use of these 2 types of antibodies as the indicator.

FIG. 3-4 shows the results of measurement of the REIC/Dkk-3 protein concentration in the serum samples of 5 patients before treatment.

FIG. 4-1 shows the results of measurement of the REIC/Dkk-3 protein concentration in serum samples obtained from 5 prostate cancer patients, 5 healthy individuals, and 5 post-surgery patients measured via sandwich ELISA with the use of the N-1 antibody that recognizes the N-terminal domain or the Cys-3 antibody that recognizes the cysteine-rich domain as a capture antibody and the biotin-labeled anti-REIC/Dkk-3 polyclonal antibody as a detection antibody. The figure indicates that the REIC/Dkk-3 protein concentration ratio measured with the use of two types of capture antibodies can be used for prediction of cancer and determination of prognosis.

FIG. 4-2 shows the profiles of 5 prostate cancer patients subjected to measurement of the REIC/Dkk-3 protein concentration in the serum samples.

FIG. 5 shows the results of examination of an antibody that can be used in combination with the N-1 antibody that recognizes the N-terminal domain or the Cys-3 antibody that recognizes the cysteine-rich domain as a detection antibody in the sandwich ELISA system. An antibody different from the detection antibody was selected as a capture antibody, the purified REIC/Dkk-3 protein was added at 100 ng/ml and 10 ng/ml, and avidin-HRP was used as a reactive complex that reacts with the detection antibody. HRP activity serving as the indicator of the level of binding between the REIC/Dkk-3 protein and various types of antibodies is shown in terms of the absorbance at 450 nm.

DESCRIPTION OF EMBODIMENTS

Hereinafter, the present invention will be described in detail.

The present invention involves the use of an antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient.

SEQ ID NO: 1 and SEQ ID NO: 2 show the full-length nucleotide sequence of the REIC/Dkk-3 gene (the REIC gene) and the amino acid sequence of the protein encoded by the gene, respectively. In the amino acid sequence as shown in SEQ ID NO: 2, a sequence comprising amino acids 1 to 21 is a signal sequence.

Figures 1, 2:
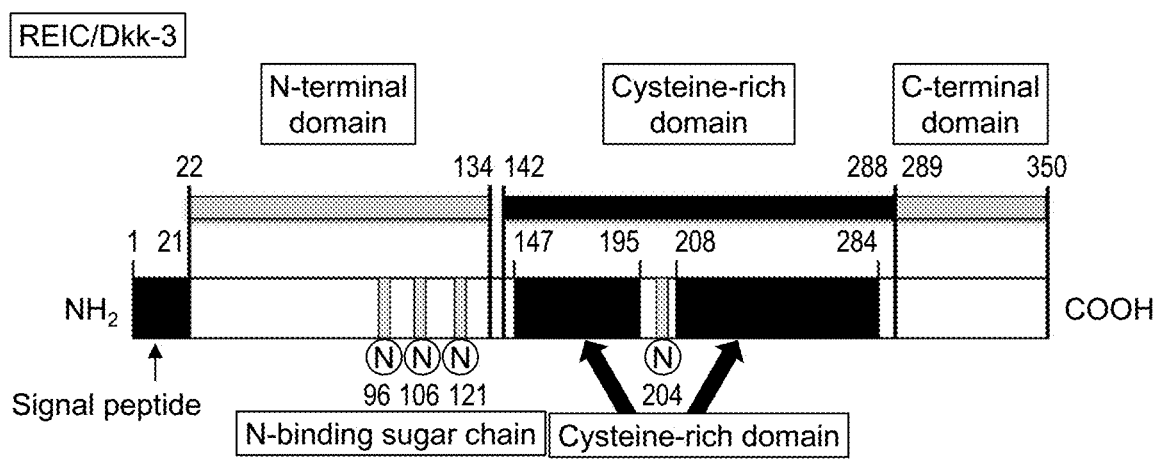
Figure 2:
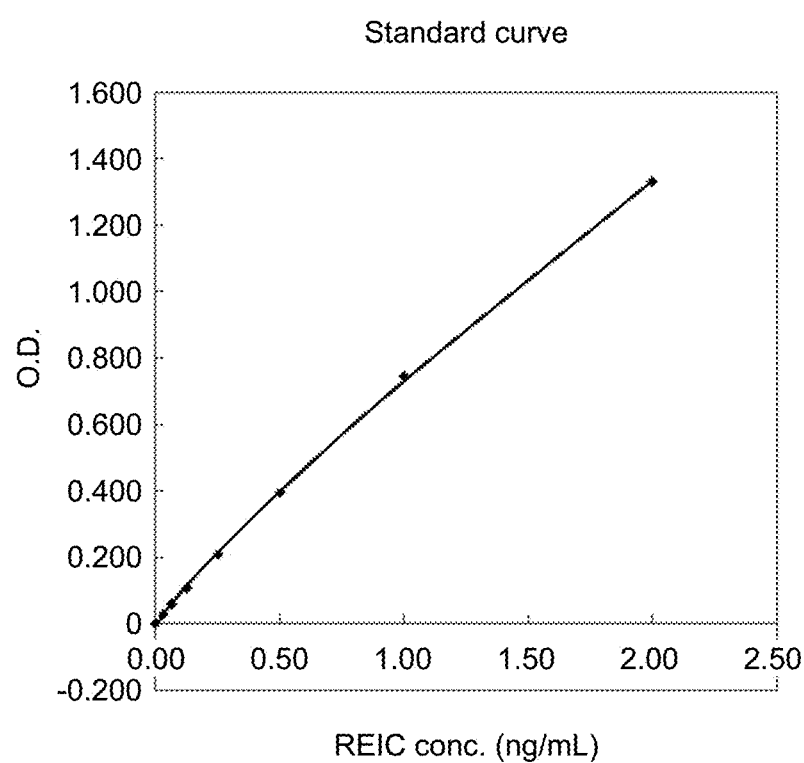

As shown in FIG. 1-2, the REIC/Dkk-3 protein comprises a N-terminal domain (a region comprising amino acids 22 to 134 in the amino acid sequence as shown in SEQ ID NO: 2), a cysteine-rich domain (a region comprising amino acids 142 to 288 in the amino acid sequence as shown in SEQ ID NO: 2), and a C-terminal domain (a region comprising amino acids 289 to 350 in the amino acid sequence as shown in SEQ ID NO: 2).

The REIC/Dkk-3 protein having an active structure is the REIC/Dkk-3 protein produced by a normal cell of a healthy individual who is not suffered from cancer.

Cancer cells do not produce or secrete the REIC/Dkk-3 protein, and the REIC/Dkk-3 protein existing at a high level in the blood from a cancer patient is considered to have abnormality in the N-terminal domain structure when the REIC/Dkk-3 protein produced and secreted by a normal cell undergoes modification, such as degradation of the N-terminal domain by other proteins produced and secreted by cancer cells (e.g., a protease or a protein binding to the REIC/Dkk-3 protein), binding of other substances to the N-terminal domain, or changes in sugar chain addition patterns of the N-terminal domain. More specifically, the REIC/Dkk-3 protein existing at a high level in the blood from a cancer patient is the REIC/Dkk-3 protein that has been modified to have a structure different from that of the REIC/Dkk-3 protein produced and secreted by a normal cell upon suffering from cancer. Alternatively, the REIC/Dkk-3 protein existing at a high level in the blood from a cancer patient can be regarded as the REIC/Dkk-3 protein that has been modified to have a structure different from that of the REIC/Dkk-3 protein produced and secreted by a normal cell in the presence of cancer cells. In contrast, the REIC/Dkk-3 protein produced by a normal cell of a healthy individual does not have abnormality in the N-terminal domain structure. In the present invention, the REIC/Dkk-3 protein that does not have abnormality in the N-terminal domain structure produced by a normal cell of a healthy individual is referred to as "the REIC/Dkk-3 protein having an active structure." Specifically, an antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is an antibody that recognizes the N-terminal domain of the REIC/Dkk-3 protein having an active structure produced by a normal cell. More specifically, an antibody that recognizes the N-terminal domain of the REIC/Dkk-3 protein having an active structure produced by a normal cell has low reactivity with the REIC/Dkk-3 protein molecular species existing at a high level in the blood from a cancer patient and it can recognize a particular REIC/Dkk-3 protein molecular species having an active structure in the blood. It can recognize a difference between the structure of the REIC/Dkk-3 protein molecule peculiar to the serum obtained from a cancer patient and the structure of the REIC/Dkk-3 protein molecule in the serum obtained from a healthy individual. As described below, the N-1 antibody, which is an anti-REIC/Dkk-3 protein monoclonal antibody, is an antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient. Accordingly, the REIC/Dkk-3 protein existing at a high level in the blood from a cancer patient is also referred to as "the REIC/Dkk-3 protein having lower reactivity with the N-1 antibody."

In order to detect the REIC/Dkk-3 protein having an active structure separately from the REIC/Dkk-3 protein existing at a high level in the blood from a cancer patient, in the present invention, an antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient can be used in adequate combination with an antibody that specifically recognizes the REIC/Dkk-3 protein having an active structure produced by a normal cell and the REIC/Dkk-3 protein existing at a high level in the blood from a cancer patient. An antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is an antibody that recognizes the N-terminal domain of REIC/Dkk-3, which is also referred to as "the first antibody." An antibody that specifically recognizes the REIC/Dkk-3 protein having an active structure produced by a normal cell and the REIC/Dkk-3 protein existing at a high level in the blood from a cancer patient is an antibody that recognizes the cysteine-rich domain or an antibody that recognizes the C-terminal domain, which is also referred to as "the second antibody."

A protein comprising an amino acid sequence from Ala at position 22 to Ile at position 350 of the amino acid sequence as shown in SEQ ID NO: 2 is referred to as the full-length REIC/Dkk-3 protein (Ala22-Ile350), a partial region comprising the cysteine-rich domain of an amino acid sequence from Ser at position 135 to Phe at position 288 is referred to as the REIC partial region 3 (Ser135-Phe288), and a partial region comprising an amino acid sequence from Arg at position 142 to Ile at position 350 is referred to as the REIC partial region 1 (Arg142-Ile350) (WO 2012/002582).

The anti-REIC/Dkk-3 antibody of the present invention may be prepared with the use of the full-length REIC/Dkk-3 protein as an immunogen, and a fragment of the REIC/Dkk-3 protein, such as the REIC partial region 1 (Arg142-Ile350) or the REIC partial region 3 (Ser135-Phe288), may be used as an immunogen. As the full-length REIC/Dkk-3 protein as an immunogen, the REIC/Dkk-3 protein having an active structure, specifically, a recombinant REIC/Dkk-3 protein or a REIC/Dkk-3 protein produced by a normal cell may be used. The region recognized by the obtained antibody can be determined on the basis of reactivity with the full-length REIC/Dkk-3 protein, the REIC partial region 3 (Ser135-Phe288), and the REIC partial region 1 (Arg142-Ile350). An antibody that recognizes the N-terminal domain reacts with the full-length REIC/Dkk-3 protein, but it does not react with the REIC partial region 3 or the REIC partial region 1. An antibody that recognizes the C-terminal domain reacts with the full-length REIC/Dkk-3 protein and the REIC partial region 1, but it does not react with the REIC partial region 3. An antibody that recognizes the cysteine-rich domain is an antibody other than the antibody that recognizes the N-terminal domain and the antibody that recognizes the C-terminal domain, and it reacts with the full-length REIC/Dkk-3 protein, the REIC partial region 1, and the REIC partial region 3. Specifically, an antibody that recognizes the N-terminal domain is an antibody that recognizes the partial region (Ala22-Thr134). An antibody that recognizes the C-terminal domain is an antibody that recognizes the partial region (Val289-Ile350), and antibody that recognizes the cysteine-rich domain is an antibody that recognizes the partial region (Ser142-Phe288).

In this description, the term "antibody" is used in an extensive sense. Specific examples thereof include a monoclonal antibody (including a full-length (complete) monoclonal antibody), a polyclonal antibody, a multispecific antibody (e.g., a bispecific antibody), and a functional fragment of an antibody. Use of a monoclonal antibody is preferable in the present invention. A useful antibody in accordance with the method of the present invention may be prepared via a conventional technique and/or genetic engineering.

A "functional antibody fragment" includes a part of a full-length antibody. In general, a functional antibody fragment includes an antigen-binding region or an antibody variable region, which has antigen-binding activity. Examples thereof include multispecific antibodies prepared from Fab, Fab', F(ab')$_2$, and Fv fragments, a diabody, a single-chain antibody molecule, and an antigen fragment. Also, multimers of such antibody fragments are within the scope of the functional antibody fragment of the present invention. Fab is a fragment obtained by treating an antibody with papain which is a protease, and it is an antibody fragment having an activity of binding to an antigen with a molecular weight of about 50,000 composed of an amino-terminal half of the H chain bound to the entire L chain via a disulfide bond. F(ab')$_2$ is an antibody fragment with a molecular weight of about 100,000 among fragments obtained by treating IgG with pepsin which is a protease comprising Fab bound thereto via a disulfide bond in the hinge region. Fab' is an antibody fragment with a molecular weight of about 50,000 resulting from cleavage of the disulfide bond in the hinge region of F(ab')$_2$. An Fv fragment (scFv) is an antibody fragment composed of a heavy-chain variable region (VH) linked to a light-chain variable region (VL) via a peptide linker. A diabody is an antibody fragment prepared by dimerization of scFv, which is a divalent antibody fragment having antigen-binding activity.

The functional antibody fragment can be produced via synthesis or genetic engineering on the basis of the amino acid sequence information of the anti-REIC/Dkk-3 antibody of the present invention or nucleotide sequence information of the gene encoding the anti-REIC/Dkk-3 antibody.

The term "monoclonal antibody" used herein refers to an antibody obtained from among a group consisting of substantially homogeneous antibodies; more specifically, a group of identical antibodies, excluding very small quantities of naturally occurring mutants. A monoclonal antibody is highly specific and it binds to a single antigen site. On the contrary to conventional (polyclonal) antibody products including different antibodies targeting antigen-determinants that are typically different (i.e., epitopes), in addition, each monoclonal antibody targets a single determinant on the antigen. A monoclonal antibody used in accordance with the present invention is prepared via, for example, a hybridoma technique or recombinant DNA technique. In addition, such monoclonal antibody is isolated and prepared from, for example, phage antibody library.

The term "monoclonal antibody" used herein encompasses a "chimeric antibody" (in which a part of a heavy chain and/or a light chain is an antibody derived from a particular species or identical or homologous to a corresponding sequence in an antibody of a particular antibody class or subclass and the other part of the chain is an antibody derived from another species or identical or homologous to a corresponding sequence in an antibody of a particular antibody class or subclass). In addition, the functional antibody fragment is within the scope of the monoclonal antibody, provided that such fragment exerts physiological activity of interest.

A representative example of the monoclonal antibody of the present invention is the anti-REIC/Dkk-3 protein monoclonal antibody prepared by the iliac lymph node method (JP Patent No. 4,098,796) aimed at development of the REIC/Dkk-3 protein concentration assay system. For example, such antibody is used as a clinical trial sample for identification and quantification of the REIC/Dkk-3 protein in specimens sampled in various clinical tests.

An antibody used for the REIC/Dkk-3 protein identification and quantification in the present invention may be enzyme-labeled, fluorescence-labeled, luminescence-labeled, or radioisotope (RI)-labeled. An antibody may be labeled in accordance with any conventional technique. Examples of enzyme labels include horseradish peroxidase (HRP), alkaline phosphatase, and δ-galactosidase. A biotin label may also be employed.

Examples of monoclonal antibody that recognize the N-terminal domain of the REIC/Dkk-3 protein, which is a monoclonal antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient, include the N-1 antibody and the N-2 antibody. Examples of monoclonal antibody that recognize the cysteine-rich domain of the REIC/Dkk-3 protein, which is a monoclonal antibody that specifically recognizes the REIC/

Dkk-3 protein having an active structure produced by a normal cell and the REIC/Dkk-3 protein existing at a high level in the blood from a cancer patient, include the Cys-1 antibody, the Cys-2 antibody, the Cys-3 antibody, the Cys-4 antibody, the Cys-5 antibody, the Cys-6 antibody, the Cys-7 antibody, and the Cys-8 antibody. Examples of monoclonal antibody that recognize the C-terminal domain of the REIC/Dkk-3 protein include the C-1 antibody and the C-2 antibody.

The hybridoma producing the N-1 antibody is deposited internationally as of Aug. 19, 2015 with the Patent Microorganisms Depositary of the National Institute of Technology and Evaluation (NITE) (NITE Patent Microorganisms Depository, Room 122, 2-5-8 Kazusakamatari, Kisarazu-shi, Chiba, Japan, 292-0818) under Accession Number NITE BP-02103 (ID: REIC-N-1). The hybridoma producing the Cys-3 antibody is deposited internationally as of Aug. 19, 2015 with the Patent Microorganisms Depositary of the National Institute of Technology and Evaluation (NITE) (NITE Patent Microorganisms Depository, Room 122, 2-5-8 Kazusakamatari, Kisarazu-shi, Chiba, Japan, 292-0818) under Accession Number NITE BP-02104 (ID: REIC-Cys-3).

The 12 types of antibodies according to the present invention have high specificity to and very high affinity with the REIC/Dkk-3 protein. Thus, all such antibodies are applicable to the sandwich ELISA method.

The domains on the REIC/Dkk-3 protein molecules recognized by such 12 types of antibodies have already been identified. In particular, an antibody that recognizes the cysteine-rich domain enables diagnosis applicable to monitoring of REIC/Dkk-3 treatment with the use of fragment peptides playing a role of anticancer immunological activity, in addition to the full-length chain of the REIC/Dkk-3 protein molecule.

An antibody that recognizes the N-terminal domain is capable of distinguishing the molecular structure of the REIC/Dkk-3 protein peculiar to the serum obtained from a cancer patient from the molecular structure of the REIC/Dkk-3 protein obtained from the serum sample of a healthy individual. The REIC/Dkk-3 protein is measured with the use of such antibody in combination with an antibody that recognizes the cysteine-rich domain or the C-terminal domain, and diagnosis is performed using the ratio of the measured values as the indicator. This can provide a method of diagnosis that has eliminated the false diagnosis in the diagnosis using the concentration that varies among individuals as the indicator.

In the present invention, in addition, an antibody-like molecule and an antibody-like substance are within the scope of an antibody, in addition to an antibody molecule.

The antibody-like molecule and the antibody-like substance may be a protein, compound, fragment, or the like, provided that such molecule or substance recognizes and binds to a particular active partial structure recognized by the novel antibody.

With the use of the antibody that recognizes the REIC/Dkk-3 protein of the present invention, the REIC/Dkk-3 protein in the biological sample obtained from a subject can be measured. While the biological sample derived from a subject is not particularly limited, examples thereof include blood, serum, plasma, urine, saliva, sperm, exudate from the chest, cerebral spinal fluid, ascites, pleural effusion, amnion liquid, vesical wash, and bronchoalveolar lavage. Blood, serum, and plasma are particularly preferable. A sample derived from the subject may be raw, frozen, or treated with heparin, citric acid, or EDTA.

The REIC/Dkk-3 protein in the sample derived from a subject can be detected via quantitative immunoassay techniques known to a person skilled in the art, such as immunoblotting, enzyme immunoassay (EIA), enzyme-linked immunosorbent assay (ELISA), radioimmunoassay (RIA), the dual-antibody sandwich method, aggregation, fluorescence immunoassay, or immunochromatography. Detection is preferably carried out via sandwich assay, such as sandwich ELISA, involving the use of a capture antibody and a labeled detection antibody.

In such immunoassay techniques, fluorescence-labeled antibodies, luminescence-labeled antibodies, radioisotope (RD-labeled antibodies, and the like can be used, in addition to enzyme-labeled antibodies.

In sandwich assay techniques, a capture antibody is immobilized on the surface of the carrier so as to detect or quantify the REIC/Dkk-3 protein.

Examples of carriers that can be adequately used in sandwich assay techniques include polymeric carriers, such as polypropylene, polystyrene, substituted polystyrene, polyacrylamide, and polyvinyl chloride, and examples further include glass beads, agarose, and nitrocellulose.

For example, a sandwich ELISA technique involves the use of a mouse anti-human REIC/Dkk-3 protein monoclonal antibody as a capture antibody and a biotin-labeled rabbit anti-human REIC/Dkk-3 protein polyclonal antibody as a detection antibody. A capture monoclonal antibody is immobilized on a microplate well. The REIC/Dkk-3 protein or the REIC/Dkk-3 standard antigen (the wild-type recombinant REIC/Dkk-3 protein) in the diluted human serum/plasma sample is subjected to incubation in wells to allow the REIC/Dkk-3 antigen to bind thereto with the aid of the capture monoclonal antibody. After the wells are washed, the biotin-labeled detection antibody is added to the REIC/Dkk-3 antigen immobilized with the aid of the capture antibody, and the wells are then washed again. Subsequently, the avidin-horseradish-peroxidase complex is added. After the final process of washing, a TMB substrate is added to the wells to detect the activity of the bound peroxidase. The reaction is terminated with the addition of 2N sulfuric acid and the absorbance is measured at 450 nm. The REIC/Dkk-3 protein concentration in the serum or plasma sample can be determined on the basis of the absorbance of the REIC/Dkk-3 protein-containing sample. As a capture antibody, a monoclonal antibody that specifically recognizes the N-terminal domain of the REIC/Dkk-3 protein can be used, with the use of the N-1 antibody being preferable, and a monoclonal antibody that specifically recognizes the cysteine-rich domain of the REIC/Dkk-3 protein can be used, with the use of the Cys-3 antibody being preferable. As a detection antibody, a monoclonal antibody reacting with the REIC/Dkk-3 protein or a polyclonal antibody prepared with the use of the recombinant REIC/Dkk-3 protein or the REIC/Dkk-3 protein produced by a normal cell as the immunogen can be used. Use of a monoclonal antibody is preferable since differences in reactivity would not be caused among different batches.

When quantifying the REIC/Dkk-3 protein, it is preferable that a calibration curve be prepared in advance with the use of a sample containing a known amount of the REIC/Dkk-3 protein. When detection is performed, alternatively, a plurality of control samples each containing a known amount of the REIC/Dkk-3 protein may be prepared, such control samples may be simultaneously subjected to measurement, and a calibration curve may then be prepared. On the basis of the measured value and the calibration curve, the amount of the REIC/Dkk-3 protein in the test samples can be quantified.

The REIC/Dkk-3 protein concentration in the sample obtained from a subject can serve as an indicator for evaluation of treatment effects of the REIC/Dkk-3 gene preparation or the REIC/Dkk-3 protein preparation, so as to achieve benefits of REIC/Dkk-3 treatment. Treatment involving the use of REIC/Dkk-3 is referred to as "REIC/Dkk-3 treatment."

By measuring the REIC/Dkk-3 protein in the biological sample obtained from a subject with the use of the antibody of the present invention, specifically, cancer in the subject can be detected. When the subject has already been suffered from cancer and under cancer treatment, changes in the REIC/Dkk-3 protein dynamics in the blood of the subject with time, specifically, changes in concentration of the REIC/Dkk-3 protein having an active structure and changes in concentration of the REIC/Dkk-3 protein existing at a high level in the blood from a cancer patient can be detected. Changes in the REIC/Dkk-3 protein dynamics in the blood with time reflect changes in cancer status in a cancer patient, and the cancer status can be evaluated based thereon. In the treatment involving the use of the REIC/Dkk-3 gene preparation, for example, an increase in the REIC/Dkk-3 protein concentration indicates that the REIC/Dkk-3 protein as a therapeutically effective component is expressed in a cancer cell, and expression of the REIC/Dkk-3 protein in a cancer cell indicates the effects of treatment. Specifically, changes in the EIC/Dkk-3 protein dynamics can be monitored, so that cancer treatment monitoring can be thus carried out. When the subject has cancer, in addition, prognosis of the cancer can be determined. Here, detection of cancer encompasses determination regarding whether or not a subject is suffered from cancer (including a precancer state), prediction whether or not a subject is at a risk of cancer, determination of cancer malignancy (the stage of cancer progression, the grade), and the like. By cancer treatment monitoring, cancer treatment activity or cancer treatment effects when cancer treatment is applied to a cancer patient are monitored.

In general, such evaluation, prediction, and diagnosis are performed by a physician, and the antibody of the present invention can be used to attain auxiliary data used for evaluation, prediction, and diagnosis.

In the present invention, precancer and neoplastic diseases are within the scope of cancer. Examples include cerebral/neural tumor, skin cancer, stomach cancer, lung cancer, liver cancer, lymphoma/leukemia, colonic cancer, pancreatic cancer, anal/rectal cancer, esophageal cancer, uterine cancer, breast cancer, adrenal cancer, renal cancer, pelviureteric cancer, bladder cancer, prostate cancer, urethral cancer, penile cancer, testicular cancer, osteoma/osteosarcoma, leiomyoma, rhabdomyoma, mesoepithelioma, and precancer causing the cancers mentioned above.

In the present invention, the target of cancer treatment monitoring is not limited, and examples include gene therapy involving the use of the REIC/Dkk-3 gene and a REIC/Dkk-3 gene fragment and treatment involving the use of the REIC/Dkk-3 protein and a REIC/Dkk-3 peptide fragment.

As described above, normal cells obtained from a healthy individual who is not suffered from cancer produce the REIC/Dkk-3 protein having an active structure, and the blood obtained from a patient suffered from cancer contains the REIC/Dkk-3 protein having an abnormal structure.

In the present invention, the REIC/Dkk-3 protein concentration in the sample obtained from a subject is assayed.

Alternatively, the REIC/Dkk-3 protein having an active structure produced by a normal cell in the sample obtained from a subject is assayed separately from the REIC/Dkk-3 protein existing at a high level in the blood from a cancer patient.

For example, the REIC/Dkk-3 protein in the sample obtained from a subject is assayed with the use of an antibody that specifically recognizes the N-terminal domain of the REIC/Dkk-3 protein and specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient. When a subject is suffered from cancer, the amount of the REIC/Dkk-3 protein having an active structure is decreased in the sample. An antibody that specifically recognizes the N-terminal domain, and specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient cannot recognize the REIC/Dkk-3 protein existing at a high level in the blood from a cancer patient. such antibody has low reactivity with such REIC/Dkk-3 protein. Thus, the measured REIC/Dkk-3 protein level is lowered. In contrast, an antibody that specifically recognizes both the REIC/Dkk-3 protein having an active structure produced by a normal cell and the REIC/Dkk-3 protein existing at a high level in the blood from a cancer patient, such as an antibody that recognizes the cysteine-rich domain, is also capable of recognizing the REIC/Dkk-3 protein that is present at a high level in the blood of a cancer patient. Thus, the measured REIC/Dkk-3 protein level is not lowered to a significant extent.

When the concentration of the REIC/Dkk-3 protein existing at a high level in the blood sample obtained from a target cancer patient can be measured by itself, cancer in the subject can be detected using the measured concentration as the indicator, and cancer treatment monitoring can be performed. Further, prognosis of a subject suffered from cancer can be determined. When the REIC/Dkk-3 protein concentration in the sample obtained from the subject measured with the use of an antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient is measured to be lower than 50 ng/ml, preferably 30 ng/ml, and more preferably 20 ng/ml, the subject can be determined to have precancer and/or a neoplastic disease. When the REIC/Dkk-3 protein concentration in the sample obtained from the subject measured with the use of an antibody that specifically recognizes and binds to the REIC/Dkk-3 protein having an active structure produced by a normal cell but does not recognize and bind to the REIC/Dkk-3 protein existing at a high level in the blood from a cancer patient or has a low degree of reactivity with the REIC/Dkk-3 protein existing at a high level in the blood from a cancer patient is lower than the REIC/Dkk-3 protein concentration in the control sample, which is obtained from a healthy individual, the subject may be evaluated as having precancer or a neoplastic disease.

On the basis of the ratio of the concentration of the REIC/Dkk-3 protein having an active structure produced by a normal cell relative to the concentration of the entire REIC/Dkk-3 proteins (i.e., the REIC/Dkk-3 protein having an active structure produced by a normal cell and the REIC/Dkk-3 protein existing at a high level in the blood from a cancer patient) in the sample obtained from the subject, also, cancer in the subject can be detected. When the subject is suffered from cancer, in addition, cancer treatment monitoring can be carried out, and prognosis can be determined. The ratio of the concentration of the REIC/Dkk-3 protein having an active structure produced by a normal cell relative to the concentration of the entire REIC/Dkk-3 proteins may be the ratio of the concentration measured with the use of an antibody that specifically recognizes and binds to the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient relative to the concentration measured with the use of an antibody that specifically recognizes the REIC/Dkk-3 protein having an active structure produced by a normal cell and the REIC/Dkk-3 protein existing at a high level in the blood from a cancer patient. For example, the ratio of the concentration measured with the use of an antibody that recognizes the N-terminal domain of the REIC/Dkk-3 protein relative to the concentration measured with the use of an antibody that recognizes the cysteine-rich domain of the REIC/Dkk-3 protein may be employed. The antibody that recognizes the N-terminal domain of the REIC/Dkk-3 protein cannot recognize the REIC/Dkk-3 protein existing at a high level in the blood from a cancer patient or such antibody has low of reactivity with such protein. The antibody that recognizes the cysteine-rich domain of the REIC/Dkk-3 protein can recognize both the REIC/Dkk-3 protein existing at a high level in the blood from a cancer patient and the REIC/Dkk-3 protein having an active structure produced by a normal cell. An assay involving the use of an antibody that recognizes the N-terminal domain of the REIC/Dkk-3 protein can be carried out via the sandwich ELISA method involving the use of, for example, an antibody that recognizes the N-terminal domain of the REIC/Dkk-3 protein as a capture antibody and, as a detection antibody, a polyclonal antibody prepared using the full-length REIC/Dkk-3 as an immunogen. Also, a monoclonal antibody that recognizes the cysteine-rich domain or the C-terminal domain of the REIC/Dkk-3 protein can be used as a detection antibody instead of the polyclonal antibody. An assay involving the use of an antibody that recognizes the cysteine-rich domain of the REIC/Dkk-3 protein can be carried out via the sandwich ELISA method involving the use of, for example, an antibody that recognizes the cysteine-rich domain of the REIC/Dkk-3 protein as a capture antibody and, as a detection antibody, a polyclonal antibody prepared with the use of the full-length REIC/Dkk-3 as an immunogen. Also, a monoclonal antibody that recognizes the cysteine-rich domain or the C-terminal domain of the REIC/Dkk-3 protein can be used as a detection antibody instead of the polyclonal antibody. An example of an antibody that recognizes the N-terminal domain of the REIC/Dkk-3 protein is the N-1 antibody and an example of an antibody that recognizes the cysteine-rich domain of the REIC/Dkk-3 protein is the Cys-3 antibody.

When the ratio of the concentration measured with the use of an antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient relative to the concentration of the REIC/Dkk-3 protein measured with the use of an antibody that specifically recognizes the REIC/Dkk-3 protein having an active structure produced by a normal cell and the REIC/Dkk-3 protein existing at a high level in the blood from a cancer patient is lower than the ratio determined with the use of the biological sample obtained from a healthy individual, for example, the subject can be evaluated as being at a risk of having precancer and/or a neoplastic disease.

Monitoring of cancer treatment can be carried out by periodically obtaining samples from a patient under cancer treatment, for example, before, during, or after the cancer treatment with time and assaying the REIC/Dkk-3 protein in the samples with the use of the antibodies described above. On the basis of a change in the REIC/Dkk-3 protein concentration in the periodically collected samples as the indicator, cancer treatment monitoring can be carried out.

When the concentration of the REIC/Dkk-3 protein having an active structure produced by a normal cell is elevated in the sample that is periodically obtained from a patient under cancer treatment, for example, when the REIC/Dkk-3 protein concentration measured with the use of an antibody that recognizes the N-terminal domain of the REIC/Dkk-3 protein, such as the N-1 antibody; that is, an antibody that specifically recognizes the REIC/Dkk-3 protein having an active structure produced by a normal cell but does not recognize and bind to the REIC/Dkk-3 protein existing at a high level in the blood from a cancer patient or has low reactivity with the REIC/Dkk-3 protein existing at a high level in the blood from a cancer patient, is elevated, such elevation indicates that REIC/Dkk-3 is expressed in a cancer cell, and REIC/Dkk-3 expression in a cancer cell indicates that REIC/Dkk-3 exerts treatment activity or treatment effects. Thus, disease remission or a positive response to cancer treatment is observed, and effects of cancer treatment are approved. When the concentration of the REIC/Dkk-3 protein having an active structure produced by a normal cell is lowered, in contrast, effects of cancer treatment are not approved, or the cancer stage is determined to have advanced.

When the ratio of the concentration measured with the use of an antibody that specifically recognizes the REIC/Dkk-3 protein having an active structure produced by a normal cell but has low reactivity with the REIC/Dkk-3 protein existing at a high level in the blood from a cancer patient relative to the concentration of the REIC/Dkk-3 protein measured with the use of an antibody that specifically recognizes the REIC/Dkk-3 protein having an active structure produced by a normal cell and the REIC/Dkk-3 protein existing at a high level in the blood from a cancer patient is elevated, for example, disease remission or a positive response to cancer treatment is observed, and effects of cancer treatment are approved. When the ratio is lowered, in contrast, effects of cancer treatment are not approved, or the cancer stage is determined to have advanced.

The results of cancer treatment monitoring according to the method of the present invention can be used as additional information for determination of an optimal treatment method for a cancer patient or for selection by a patient who is to undergo cancer treatment with REIC/Dkk-3. Specifically, the method of the present invention is also useful for companion diagnostics. The term "companion diagnostics" used herein refers to a clinical test that is carried out to predict the efficacy or side effects of pharmaceutical products before administration thereof.

A method for selecting treatment comprises immunologically detecting and quantifying the average concentration of the REIC/Dkk-3 protein having an active structure in the samples obtained from control groups, immunologically detecting and quantifying gradual changes in the REIC/Dkk-3 protein concentration in the equivalent sample obtained from a patient with time, and comparing the REIC/Dkk-3 protein concentration in the sample from the patient with that in the control samples. On the basis of differences between the REIC/Dkk-3 protein concentration in the sample obtained from the patient and the average concentration in the control samples and gradual changes in the REIC/Dkk-3 protein concentration in the sample obtained from the patient, whether a conventional treatment and/or REIC/Dkk-3 treatment would be provided for the patient is determined.

The present invention encompasses a test kit for detecting cancer comprising an antibody specific to the REIC/Dkk-3 protein or a test kit for monitoring the efficacy of the treatment for the patient. Examples of antibodies that recognize the REIC/Dkk-3 protein contained in the test kit include an antibody that recognizes the N-terminal domain such as the N-1 antibody, an antibody that recognizes the cysteine-rich domain such as the Cys-3 antibody, and an antibody that recognizes the C-terminal domain. The kit may further contain instructions, a detectable tag or label, a solution accelerating antibody binding, and the like.

EXAMPLES

The present invention will be specifically described in the following examples. However, these examples are not intended to limit the scope of the present invention.

Example 1

Preparation of Anti-REIC/Dkk-3 Protein Monoclonal Antibody and Determination of Recognition Site The anti-REIC/Dkk-3 protein monoclonal antibody was prepared by the iliac lymph node method with the use of the full-length REIC/Dkk-3 protein (Ala22-Ile350) or the REIC partial region 3 including the cysteine-rich domain (Ser135-Phe288) (see Patent Literature 3) as an antigen, such antibody was selected on the basis of the reactivity with the full-length REIC/Dkk-3 protein, the REIC partial region 3, and the REIC partial region 1 (Arg142-Ile350) (see Patent Literature 3), and the recognition region thereof was determined on the basis thereof. An antibody that recognizes the N-terminal domain reacts with the full-length REIC/Dkk-3 protein, but it does not react with the REIC partial region 3 or the REIC partial region 1. An antibody that recognizes the C-terminal domain reacts with the full-length REIC/Dkk-3 protein and the REIC partial region 1, but it does not react with the REIC partial region 3. An antibody that recognizes the cysteine-rich domain is other than the antibody that recognizes the N-terminal domain and the antibody that recognize the C-terminal domain, and it reacts with the full-length REIC/Dkk-3 protein, the REIC partial region 1, and the REIC partial region 3. Specifically, the antibody that recognizes the N-terminal domain is an antibody that recognizes a partial region (Ala22-Thr134). The antibody that recognizes the C-terminal domain is an antibody that recognizes a partial region (Val289-Ile350). The antibody that recognizes the cysteine-rich domain is an antibody that recognizes a partial region (Ser142-Phe288). FIG. 1-1 shows the reaction patterns of the 12 types of antibodies selected by the method described above (i.e., N-1, N-2, C-1, C-2, Cys-1, Cys-2, Cys-3, Cys-4, Cys-5, Cys-6, Cys-7 and Cys-8 antibodies) with the antigens in terms of protein types and regions recognized by proteins. FIG. 1-2 schematically shows the REIC/Dkk-3 protein structure.

Example 2

Sandwich ELISA Targeting Human Serum and Plasma Samples

Examples of adequate assay samples for ELISA using the anti-REIC/Dkk-3 protein antibody include human plasma and human serum samples treated with heparin, citrate, and EDTA. In order to avoid assay interference caused by interfering factors that may be present in the blood, special discretion is required to prepare and assay human serum and plasma samples. Aggregates that are assumed to be contained at the time of sampling should be removed from the sample via microcentrifugation before dilution and the initial concentration of the serum and plasma samples subjected to the test should be approximately 2% or lower.

Assay Method

The human REIC/Dkk-3 protein concentration in the human plasma or serum was assayed by the sandwich ELISA method in accordance with the procedure described below.

1. As a capture antibody, the N-1 antibody that recognizes the N-terminal domain of the REIC/Dkk-3 protein is added at 50 μl/well to a microplate. The plate is subjected to the reaction at room temperature for 1 hour or at 4° C. overnight.
2. A plate wash solution is prepared.
3. Wells are washed with the plate wash solution at 200 μl/well 4 times.
4. A blocking reagent (e.g., skimmed milk/commercially available blocking agent) is added at 200 μl/well to the microplate. The plate is subjected to the reaction at room temperature for 1 hour.
5. Wells are washed with the plate wash solution at 200 μl/well 4 times.
6. The sample diluted in advance, the control sample, and 8 types of REIC/Dkk-3 protein standard samples (0 to 2,000 pg/ml) are each added at 50 μl/well to the microplate. The plate is subjected to the reaction at room temperature for 3 hours or at 4° C. overnight.
7. Wells are washed with the plate wash solution at 200 μl/well 4 times.
8. A detection antibody (e.g., a biotin-labeled anti-REIC/Dkk-3 protein polyclonal antibody) is added at 50 μl/well to the microplate. The plate is subjected to the reaction at room temperature for 1 hour.
9. Wells are washed with the plate wash solution at 200 μl/well 4 times.
10. A reactive complex (e.g., HRP-labeled avidin) that reacts with a detection antibody is added at 50 μl/well to the microplate. The plate is subjected to the reaction at room temperature for 1 hour.
11. Wells are washed with the plate wash solution at 200 μl/well 4 times.
12. A reactive substrate (e.g., a TMB substrate) is prepared and added at 50 μl/well to the microplate.
13. When the reaction proceeds sufficiently, a terminator solution is added at 100 μl/well to the microplate. 14. The absorbance at 450 nm is assayed in each well using a spectroscopic plate reader.

Calibration Curve

A calibration curve was prepared using REIC/Dkk-3 protein standard samples (the recombinant human REIC/Dkk-3 protein) at 8 different concentrations (0, 31.3, 62.5, 125, 250, 500, 1000, and 2000 pg/ml), and quantitative analysis was carried out. The calibration curve is shown in FIG. 2.

Human Serum and Plasma Samples

The serum or plasma samples were obtained from the patient before, during, and after the REIC/Dkk-3 gene therapy and cryopreserved before measurement.

Example 3

Figure 3:
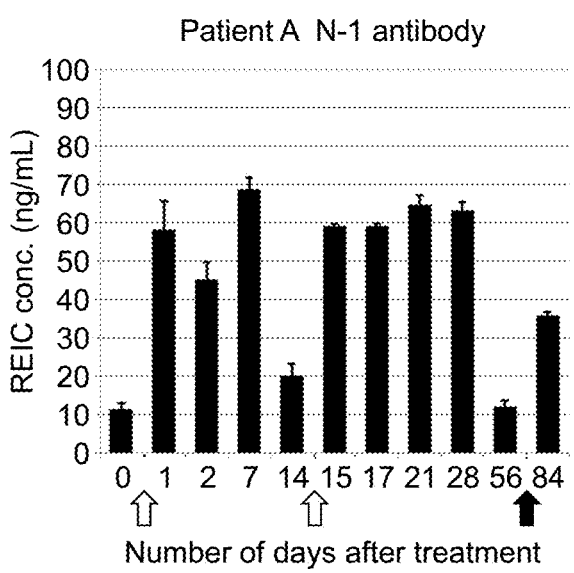
Figure 1:
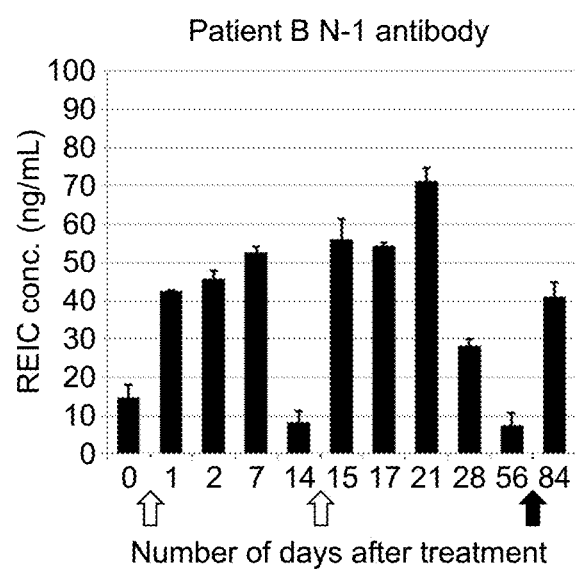
FIG. 1-1 shows the reaction patterns of the 12 types of anti-REIC/Dkk-3 monoclonal antibodies to antigens by protein types and regions recognized by the antibodies. Anti-REIC/Dkk-3 monoclonal antibodies were prepared with the use of the full-length REIC/Dkk-3 protein (Ala22-Ile350) or the REIC partial region 3 comprising a cysteine-rich domain (Ser135-Phe288) (see Patent Literature 3) as an antigen by the iliac lymph node method, the 12 types of antibodies were selected on the basis of the reactivity with the full-length REIC/Dkk-3 protein, the REIC partial region 3, and the REIC partial region 1 (Arg142-Ile350) (see Patent Literature 3), and recognition regions thereof were determined.
Figure 3:
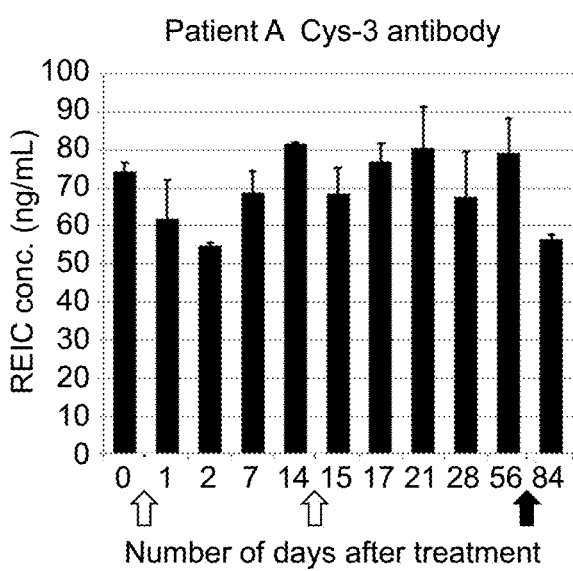
Figure 2:
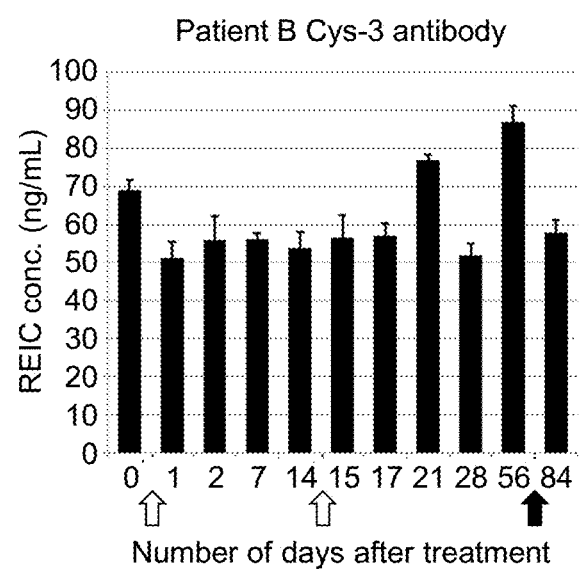
Figure 3:
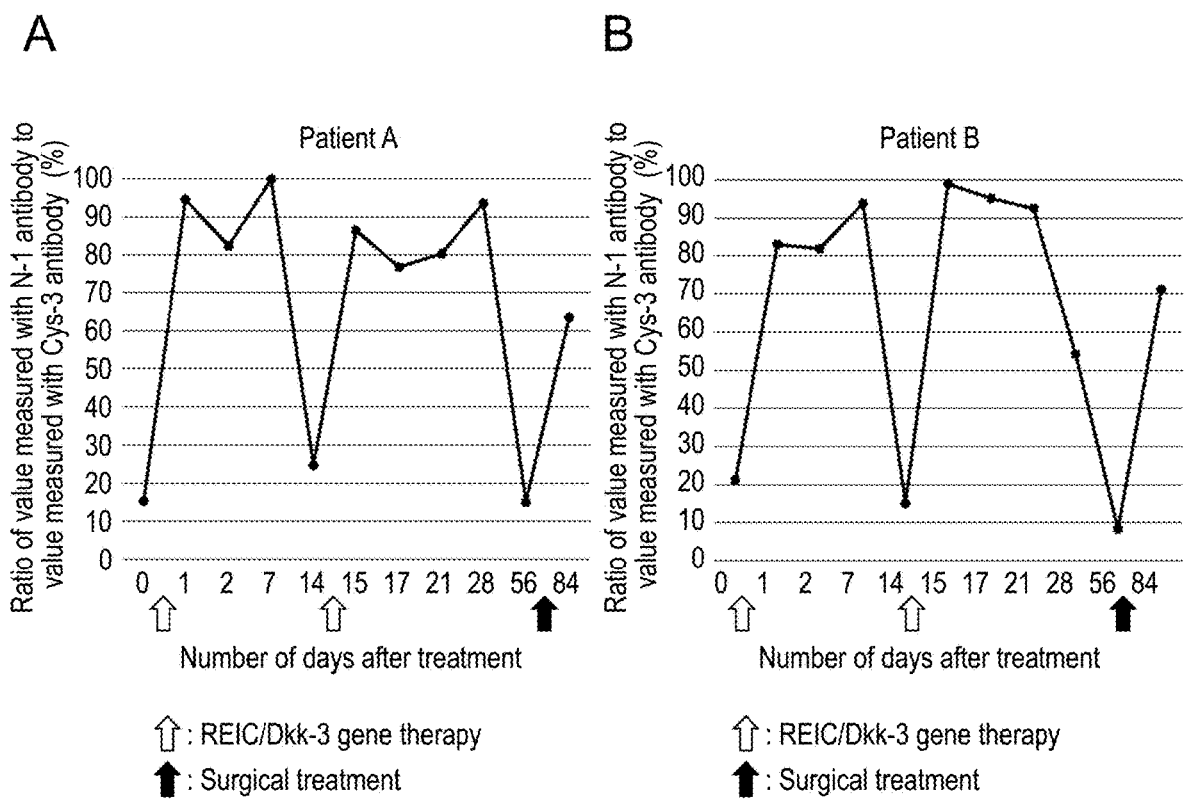
Figures 3, 4:
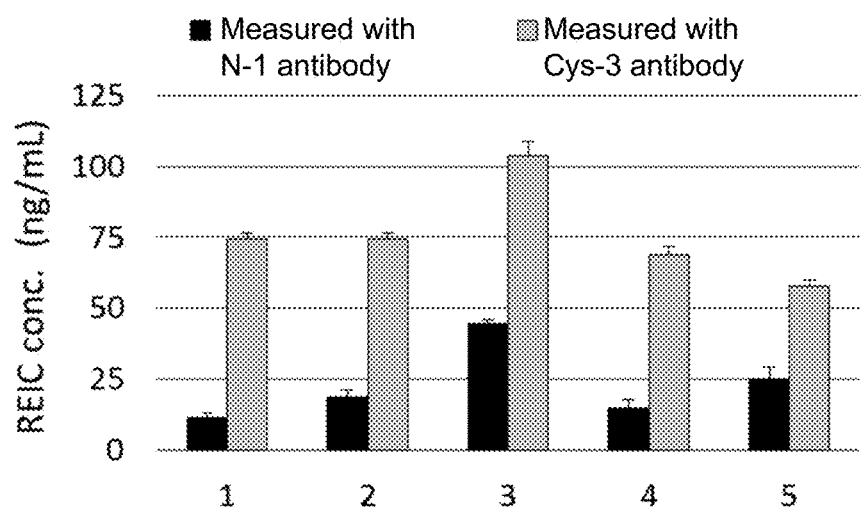
Figures 1, 4:
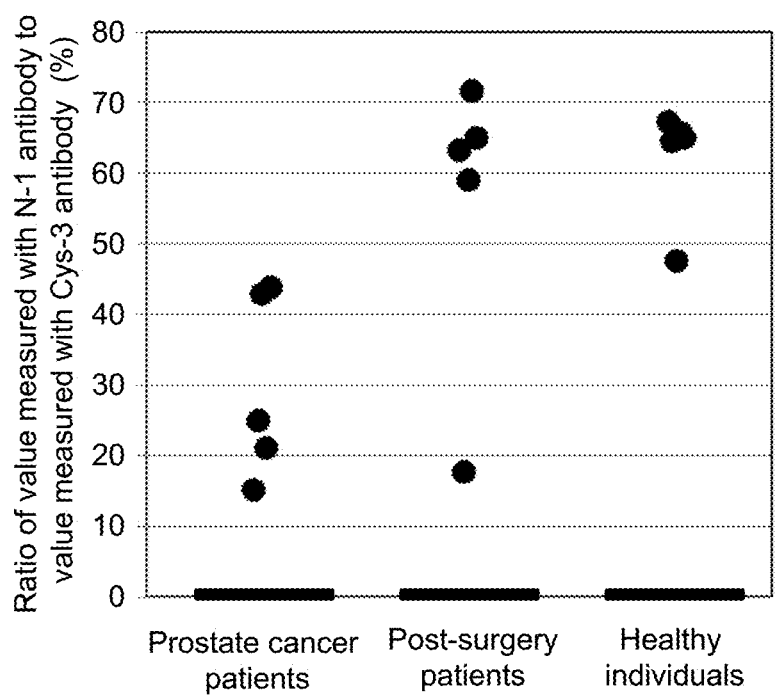

Monitoring of Treatment Via Sandwich ELISA Targeting Serum Obtained from Prostate Cancer Patient The REIC/Dkk-3 protein concentration in the serum sample obtained from a prostate cancer patient was assayed via the sandwich ELISA method. With the use of the N-1 antibody that recognizes the N-terminal domain or the Cys-3 antibody that recognizes the cysteine-rich domain as a capture antibody, the REIC/Dkk-3 protein concentration in the 11 serum samples obtained from the patient subjected to REIC/Dkk-3 gene therapy two times (0 day and 14 days after the initiation of therapy); that is, the standard serum sample (before treatment), 1, 2, 7, and 14 days after the first treatment (immediately before the second treatment), 15, 17, 21, 28, and 56 days after the first treatment (immediately before surgery), and 84 days after the initiation of therapy was measured. As a detection antibody, a biotin-labeled anti-REIC/Dkk-3 protein polyclonal antibody was used. This polyclonal antibody was prepared with the use of, as an immunogen, the REIC/Dkk-3 protein secreted from the HEK 293 cells. The results of assays demonstrate that monitoring of treatment effects can be performed with the use of the N-1 antibody that recognizes the N-terminal domain as a capture antibody. FIG. 3-1A and FIG. 3-1B show the measured data of 2 patients (Patient A and Patient B). In addition, the results of measurement of the REIC/Dkk-3 protein concentration in the serum sample with the use of the Cys-3 antibody that recognizes the cysteine-rich domain as a capture antibody are shown in FIG. 3-2A (Patient A) and FIG. 3-2B (Patient B). When the N-1 antibody was used as a capture antibody, as shown in FIG. 3-1, the REIC/Dkk-3 protein level in the serum was significantly elevated after the REIC/Dkk-3 gene therapy or surgical treatment was performed. When the Cys-3 antibody was used as a capture antibody, in contrast, the REIC/Dkk-3 protein level in the serum was not elevated after the REIC/Dkk-3 gene therapy or surgical treatment was performed. By comparing two types of the measured data obtained with the use of different capture antibodies, the reactivity of the N-1 antibody to the REIC/Dkk-3 protein in the serum obtained from a cancer patient is considered to lower to a significant extent. FIG. 3-3 shows the ratio (%) of the concentration of the REIC/Dkk-3 protein measured with the use of the N-1 antibody as a capture antibody relative to the concentration of the REIC/Dkk-3 protein measured with the use of the Cys-3 antibody as a capture antibody (concentration measured with N-1 antibody/concentration measured with Cys-3 antibody). The results demonstrate that, as the ratio (%) of the REIC/Dkk-3 protein concentration, the N-1 antibody/Cys-3 antibody value accurately reflects the dynamics of the REIC/Dkk-3 protein in the blood. FIG. 3-4 shows the results of measurement of the REIC/Dkk-3 protein concentration in the serum samples of 5 patents (Patient A, Patient B, and other 3 patients) before treatment. FIG. 3-4 shows the results of measurement when the N-1 antibody that recognizes the N-terminal domain or the Cys-3 antibody that recognizes the cysteine-rich domain is used as a capture antibody. As shown in FIG. 3-4, the REIC/Dkk-3 protein concentration in the serum measured with the use of the N-1 antibody was about 10 to 50 ng/ml, and that measured with the use of the Cys-3 antibody was about 55 to 110 ng/ml. On the basis of FIG. 3-3 and FIG. 3-4, a change in the REIC/Dkk-3 protein dynamics in the blood obtained from the post-treatment patient with time; specifically, a change in the concentration of the REIC/Dkk-3 protein having an active structure and that of the REIC/Dkk-3 protein existing at a high level in the blood from a cancer patient, can be determined using the ratio of the concentration of the REIC/Dkk-3 protein in the serum relative to the concentration measured with the use of the 2 types of antibodies described above as the indicator. A change in the REIC/Dkk-3 protein dynamics in the blood with time reflects a change in the cancer status in a cancer patient, and treatment monitoring can be carried out based thereon. While a conventional technique of diagnosis using tumor markers includes individual differences since evaluation is based on the absolute concentration in the blood of the cancer patient, the method of diagnosis according to the present invention comprises detecting a change in the REIC/Dkk-3 protein structure in the serum of the cancer patient with the use of 2 types of antibodies. Thus, the method of diagnosis according to the present invention can be a novel method of tumor diagnosis that enables tailor-made medicine that provides an optimal method of treatment for an individual patient.

Example 4

Prediction of Disease Via Comparison of Serum Obtained from Prostate Cancer Patient, Serum after Surgical Treatment, and Normal Human Serum Sandwich ELISA was carried out using the N-1 antibody that recognizes the N terminus or the Cys-3 antibody that recognizes the cysteine-rich domain as a capture antibody and the biotin-labeled anti-REIC/Dkk-3 protein polyclonal antibody used in Example 3 as a detection antibody to measure the REIC/Dkk-3 protein concentration in the serum samples obtained from the subjects: i.e., 5 prostate cancer patients, 5 post-surgery patients, and 5 healthy individuals. FIG. 4-1 shows the ratio (%) of the REIC/Dkk-3 protein concentration measured with the use of the N-1 antibody relative to that measured with the use of the Cys-3 antibody as capture antibodies (concentration measured with N-1 antibody/concentration measured with Cys-3 antibody). FIG. 4-2 shows the profiles of the 5 prostate cancer patients. As shown in FIG. 4-1, the ratio of the concentration measured with the N-1 antibody relative to the concentration measured with the Cys-3 antibody was low in the serum samples obtained from prostate cancer patients, and the ratio of the concentration measured with N-1 antibody relative to the concentration measured with the Cys-3 antibody was high in the serum samples obtained from 5 prostate cancer patients after treatment and in the serum samples obtained from healthy individuals. The results demonstrate that the ratio of the REIC/Dkk-3 protein concentrations measured with the use of the 2 types of capture antibodies can be used for prediction of cancer and determination of prognosis.

Example 5

Examination of Capture Antibody-Detection Antibody Combination Used in Sandwich ELISA System Using Anti-REIC/Dkk-3 Protein Monoclonal Antibody Capture antibodies that could be used in combination with the biotin-labeled N-1 antibody that recognizes the N terminus or the biotin-labeled Cys-3 antibody that recognizes the cysteine-rich domain as a detection antibody in the sandwich ELISA system involving the use of anti-REIC/Dkk-3 protein monoclonal antibodies (i.e., N-1, N-2, C-1, C-2, Cys-1, Cys-2, Cys-3, Cys-4, Cys-5, and Cys-6 antibodies) were examined. An antibody different from the detection antibody was selected as a capture antibody, the purified recombinant REIC/Dkk-3 protein was added at 100 ng/ml and 10 ng/ml, and avidin-HRP was used as a reactive complex that reacts with the detection antibody. FIG. 5 shows HRP activity serving as the indicator of the level of binding between the REIC/Dkk-3 protein and various types of antibodies in terms of the absorbance at 450 nm. As shown in FIG. 5, it was possible to assay the REIC/Dkk-3 protein with the use of a capture antibody and a detection antibody in any combination. It was also found that the N-1 antibody was superior to the N-2 antibody as a capture antibody and the Cys-3 antibody was superior to other antibodies that recognize the cysteine-rich domain.

INDUSTRIAL APPLICABILITY

The anti-REIC/Dkk-3 antibody of the present invention enables monitoring of cancer treatment effects involving the use of REIC/Dkk-3 gene and REIC/Dkk-3 protein medicine. Diagnosis via an immunoassay technique using the anti-REIC/Dkk-3 antibody can be used for prediction of cancer, determination of prognosis, and companion diagnostics, and such method of diagnosis is provided in the form of a test kit.

Accession Numbers:
NITE BP-02103
NITE BP-02104

All publications, patents, and patent applications cited herein are incorporated herein by reference in their entirety.

The invention claimed is:

1. A method for detecting cancer in a subject comprising
   (a) contacting a biological sample obtained from the subject with a first antibody produced by a hybridoma deposited under Accession Number NITE BP-02103 (the N-1 antibody) or an antigen-binding fragment thereof, wherein the first antibody
      (i) specifically recognizes REIC/Dkk-3 protein having an active structure produced by a normal cell, and
      (ii) does not bind to or has low reactivity with REIC/Dkk-3 protein that is present at a high level in blood from a cancer patient; and
   (b) detecting precancer or a neoplastic disease when the REIC/Dkk-3 protein levels in the biological sample from the subject are lower compared to a biological sample obtained from a healthy individual.

2. The method according to claim 1 comprising
   (a) contacting the biological sample obtained from the subject with a second antibody produced by a hybridoma deposited under Accession Number NITE BP-02104 (the Cys-3 antibody) or an antigen-binding fragment thereof, wherein the second antibody specifically recognizes REIC/Dkk-3 protein having an active structure produced by a normal cell and REIC/Dkk-3 protein that is present at a high level in blood from a cancer patient,
   (b) determining a ratio of the REIC/Dkk-3 protein concentration measured using the first antibody or antigen-binding fragment thereof relative to the REIC/Dkk-3 protein concentration measured using the second antibody or antigen-binding fragment thereof, and
   (c) detecting precancer or a neoplastic disease in the subject when the determined ratio is lower compared to a biological sample obtained from a healthy individual.

3. The method according to claim 1, wherein the first antibody specifically recognizes the N-terminal domain of REIC/Dkk-3 protein.

4. The method according to claim 2, wherein the second antibody recognizes the cysteine-rich domain of REIC/Dkk-3 protein.

* * * * *